United States Patent
Yamka et al.

(10) Patent No.: US 9,254,277 B2
(45) Date of Patent: *Feb. 9, 2016

(54) PET FOOD COMPOSITIONS AND METHODS FOR TREATING ARTHRITIS AND INFLAMMATION ASSOCIATED WITH ARTHRITIS

(75) Inventors: Ryan Michael Yamka, Succasunna, NJ (US); Nolan Zebulon Frantz, Andover, NJ (US); Samer Al-Murrani, Topeka, KS (US)

(73) Assignee: HILLS'S PET NUTRITION, INC., Topeka, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/997,361

(22) PCT Filed: Nov. 30, 2011

(86) PCT No.: PCT/US2011/062528
§ 371 (c)(1),
(2), (4) Date: Jun. 24, 2013

(87) PCT Pub. No.: WO2012/087512
PCT Pub. Date: Jun. 28, 2012

(65) Prior Publication Data
US 2013/0274335 A1    Oct. 17, 2013

Related U.S. Application Data

(60) Provisional application No. 61/426,633, filed on Dec. 23, 2010.

(51) Int. Cl.
| | | |
|---|---|---|
| *A61K 31/20* | (2006.01) | |
| *A61K 31/015* | (2006.01) | |
| *A23K 1/18* | (2006.01) | |
| *A23K 1/16* | (2006.01) | |

(52) U.S. Cl.
CPC .............. *A61K 31/20* (2013.01); *A23K 1/1603* (2013.01); *A23K 1/164* (2013.01); *A23K 1/1609* (2013.01); *A23K 1/1846* (2013.01); *A61K 31/015* (2013.01)

(58) Field of Classification Search
None
See application file for complete search history.

(56) References Cited

U.S. PATENT DOCUMENTS

| | | | |
|---|---|---|---|
| 6,055,936 A | 5/2000 | Collin | |
| 6,133,323 A * | 10/2000 | Hayek | 514/725 |
| 6,596,303 B1 | 7/2003 | Bui et al. | |
| 6,669,975 B1 | 12/2003 | Abene et al. | |
| 6,914,071 B2 * | 7/2005 | Zicker et al. | 514/440 |
| 2006/0228448 A1 | 10/2006 | Boileau et al. | |
| 2008/0233248 A1 * | 9/2008 | Swenke et al. | 426/231 |
| 2009/0182032 A1 * | 7/2009 | Zicker et al. | 514/440 |
| 2011/0269827 A1 | 11/2011 | Frantz | |

FOREIGN PATENT DOCUMENTS

| | | |
|---|---|---|
| EP | 1602284 | 12/2005 |
| WO | WO 2004/000333 | 12/2003 |
| WO | WO 2005/025322 A2 * | 3/2005 |
| WO | WO 2006/110407 | 10/2006 |
| WO | WO 2011/011472 | 1/2011 |

OTHER PUBLICATIONS

Nutritional Information for Paprika (http://nutritiondata.self.com/facts/spices-and-herbs/198/2#; Accessed Jan. 30, 2015).*
Association of American Feed Control Officials (AAFCO) Official Publication (2003, pp. 126-140).*
Shao Bin, etc. 2008, "Sources, Components, and Functions of Carotenes", China Food Additives 5:41-44 (Abstract only in English).
May 1994, "Palm Oil Carotenoids," Food and Nutrition Bulletin 15(2): retrieved from website http://archive.unu.edu/unupress/food/8F152e/8F152E05.htm.
International Search Report and Written Opinion in International Application No. PCT/US2011/062528, mailed Feb. 15, 2012.
Written Opinion in International Application No. PCT/US2011/062528, mailed Dec. 14, 2012.

* cited by examiner

*Primary Examiner* — James D Anderson

(57) ABSTRACT

The present invention provides food compositions that are effective in treating arthritis or inflammation associated with arthritis in a companion animal, preferably a canine or feline.

12 Claims, No Drawings

PET FOOD COMPOSITIONS AND METHODS FOR TREATING ARTHRITIS AND INFLAMMATION ASSOCIATED WITH ARTHRITIS

CROSS-REFERENCE TO RELATED APPLICATIONS

This application is a National Stage of International Application No. PCT/US11/62528, filed on Nov. 30, 2011, which claims the benefit of U.S. Provisional Application No. 61/426,633, filed on Dec. 23, 2010.

FIELD OF THE INVENTION

The present invention relates to pet food compositions and methods for treating arthritis and inflammation associated with arthritis in a companion animal, particularly canines and felines.

BACKGROUND OF THE INVENTION

Rheumatism and arthritis are general terms for acute and chronic conditions characterized by inflammation and pain. Rheumatism is a general category of conditions characterized by inflammation and pain in muscle and joints, including, arthritis. Arthritis is characterized by inflammation of joints that causes swelling and pain. Types of arthritis include osteoarthritis, rheumatoid arthritis, ankylosing spondylitis (AS), and systemic lupus erythematosus. The cause of such diseases is not always fully understood but may be the result of other degenerative diseases, trauma or auto-immune diseases.

Inflammation refers to a protective attempt by an organism to remove art injurious stimulus and initiate the healing processes for the tissue affected by the injurious stimulus. Inflammation occurs as a defensive response to host invasion by foreign agents and mechanical trauma that results in an immune response, microbial agents such as bacterial and viruses, toxins and neoplasia. Inflammation can be classified as either acute or chronic. Acute inflammation is an initial response to harmful stimuli and is achieved by the increased movement of plasma and leukocytes from the blood into the injured tissues. A cascade of biochemical events propagates and matures the inflammatory response, involving the local vasculature, the immune system, and various cells within the injured tissue. Chronic inflammation, or prolonged inflammation, leads to a progressive shift in the type of cells, which are present at the site of inflammation, and is characterized by simultaneous destruction and healing of the tissue from the inflammatory process.

Prior methods for preventing and treating inflammatory diseases have generally focused on oral medications such as steroidal cortisone derivatives and numerous non-steroidal anti-inflammatory drugs (NSAIDS). Unfortunately, these drugs have undesirable side effects. Other efforts have focused on joint, implants such as knee or hip implants. These methods involve lengthy and costly surgical procedures that three the patient to undergo invasive surgery with a significant recovery period.

Given the problems with current methods for treating, arthritis and inflammation associated with arthritis, there is a continuing need for new methods and compositions useful for treating arthritis and inflammation associated with arthritis and in particular, for food compositions effective in managing these conditions

BRIEF SUMMARY OF THE INVENTION

The invention advantageously provides an effective functional food-based approach to treat arthritis and inflammation associated with arthritis. The invention is characterized by the use of a combination of myristic acid and beta-carotene in a nutritionally complete pet food composition, such as a nutritionally complete canine or feline food composition. A food composition of the invention may, for example, include a combination of tomato pomace, coconut oil and carrot powder.

One embodiment of the invention provides a pet food composition that includes a myristic acid source and a beta-carotene source, in amounts effective to treat arthritis and inflammation associated with arthritis. The myristic acid source may, for example, include or consist of coconut oil, and the beta-carotene source may include or consist of at least one of tomato pomace and carrot powder.

A related embodiment of the invention provides a method for treating arthritis and inflammation associated with arthritis in a companion animal such as a canine or a feline, which includes feeding to a companion animal in need of such treatment a composition of the invention. The composition may, for example, be fed to the animal as its primary or sole nutritionally complete food on a daily basis.

Another embodiment of the invention provides the use of a myristic acid source and a beta-carotene source for the manufacture of a pet food composition, such as a nutritionally complete food, for the treatment of arthritis and inflammation associated with arthritis in a companion animal, such as a canine or a feline.

A still further embodiment of the invention provides the use of a myristic acid source and a beta-carotene source for the manufacture of a pet food composition, such as a nutritionally complete food, for the treatment of arthritis and inflammation associated with arthritis in a companion animal, such as a canine or a feline.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

As used herein, "an amount effective", "an effective amount", and like terms refer to that amount of a compound, material or composition as described herein that may be effective to achieve a particular biological result. Such results may include, but are not limited to, treatment of arthritis or inflammation associated with arthritis. Such effective activity may be achieved, for example, by administration of compositions of the present invention to an animal. An effective amount may be based on several factors, including an animal's ideal weight and frequency of feeding the animal compositions of the present invention, once, twice, or three times daily, and other compositions fed to the animal.

As used herein, the term primary food composition means the main, nutritionally comprehensive meal food that the canine or feline is fed day to day.

As contemplated herein, the compositions of the present invention are meant to encompass nutritionally complete and balanced animal food compositions. A "nutritionally complete diet" is a diet that includes sufficient nutrients for maintenance of normal health of a healthy animal on the diet. Nutritionally complete and balanced pet food compositions are familiar to one of skill in the art. For example, substances such as nutrients and ingredients suitable for nutritionally complete and balanced animal feed compositions, and recommended amounts thereof may be found for example, in the Official Publication of The Association of American Feed Control Officials, Inc. (AAFCO), Atlanta, Ga., 2005.

For example, a nutritionally complete and balanced dog food composition of the present invention may comprise: about 0 to about 90%, preferably about 5% to 60%, weight of carbohydrates; about 5% to about 70%, preferably about 1 to about 60%, more preferably about 20% to about 50%, by weight of protein; about 1% to about 50%, preferably about 2% to about 40%, more preferably about 3% to about 15%, by weight of fat; about 0.1% to about, 40%, preferably about 1% to about 30%, more preferably about 15% to about 50%, by weight of total dietary fiber, about 0 to about 15%, preferably about 2% to about 8%, by weight of vitamins and minerals, antioxidants, and other nutrients which support the nutritional needs of the animal.

Protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. The amount of "crude protein" in a composition disclosed herein may be determined based on the amount of nitrogen in the composition according to methods familiar to one of skill in the art. As contemplated herein, the compositions of the present invention may comprise from about 5% to about 70% protein, from about 10% to about 60% protein, from about 20% to about 50% protein, from about 25% to about 40% protein, and from about 29% to about 38% protein.

In certain embodiments, the nutritionally complete pet food compositions disclosed herein may comprise fat. Sources of fat for the compositions of the present invention can be supplied by any of a variety of sources known by those skilled in the art, including meat, meat by-products, fish oil, and plants. Plant fat sources include wheat, flaxseed, rye, barley, rice, sorghum, corn oats, millet, wheat germ, corn germ, soybeans, peanuts, and cottonseed, as well as oils derived from these and other plant fat sources. As contemplated herein, the compositions of the present invention may comprise from about 1 to about 20% fat, from about 2% to about 18% fat, from about 3%, to about 15% flu, from about 7% to about 14% fat, and from about 9% to about 12% fat.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NEE"), which may be calculated as follows: NFE=100%−moisture %−protein %−fat %−ash %−crude fiber %.

Total dietary fiber refers to components of a plant which are resistant to digestion by an animal's digestive enzymes. Total dietary fiber includes soluble and insoluble fibers. As contemplated herein, the compositions of the present invention may comprise from about 15% to about 50% total dietary fiber, from about 16% to about 45% total dietary fiber, from about 17% to about 40% total dietary fiber, from about 18% to about 35% total dietary fiber, from about 19% to about 30% total dietary fiber, and from about 20% to about 29% total dietary fiber.

Soluble fiber is resistant to digestion and absorption in the small intestine and undergoes complete or partial fermentation in the large intestine. Sources of soluble fiber may include beet pulp, guar gum, chicory root, psyllium, pectin, blueberry, cranberry, squash, apples, oats, beans, citrus, barley, or peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber.

Crude fiber includes indigestible components contained in cell walls and cell contents of plants such as grains, e.g., hulls of grains such as rice, corn, and beans.

The invention is further described in the following examples. The examples are merely illustrative and do not in any way limit the scope of the invention as described and claimed.

EXAMPLES

Example 1

General Material and Method

The animal compositions were prepared as follows: each food was kibbled and formulated in accordance with the Association of American Feed Control Officials nutrient guide for cats or dogs and balanced to meet adult maintenance requirements. The animals were cared for in accordance with Institutional Animal Care and Use Committee protocols.

Blood or serum samples were stored at −80° C. until analysis. Samples were extracted and prepared for analysis using standard solvent extraction methods. The extracted samples were split into equal parts for analysis on the GC/MS and LC/MS/MS platforms in a randomized run order. Data for each compound were normalized by calculating the median values for each run-day ("block normalization").

Data were analyzed either using SAS version 9.0 or a t-test to determine treatment differences. Paired t-test was used to determine if there were significant changes from baseline (month 0). The experimental unit was canine (dog) or feline (cat) and differences were considered significant when $P<0.05$.

Example 2

Canine (Dog) Arthritis Study

A canine arthritis feeding study was conducted to evaluate the efficacy of a test formula, Formula CA, on arthritic markers and activity in 36 arthritic and 21 normal geriatric dogs. The effect of the test formula was evaluated by actiwatch (activity), chemistry screens, CBC, blood and urine cartilage biomarkers, metabolomics, proteomics, and genomics, in the study, dogs were fed a control food for 28 days and then fed a control food (Formula CC) or the test formula, Formula CA, for an additional 28 days to evaluate changes in arthritic parameters in arthritic and normal geriatric dogs.

The study utilized 36 arthritic dogs with radiographic evidence of arthritis and a history of naturally occurring lameness and 21 geriatric normal healthy dogs with no radiographic evidence of arthritis or history of lameness.

Dogs on any medication were weaned from medication during the washout period at least 7 days before day 0 of the treatment period to ensure that baseline samples collected were indicative of the true condition of the dogs.

During the 28 day test period, blood samples were collected at days 0 and 28 for analysts of serum chemistry, CBC, blood and urine biomarkers, genomics, proteomics, and metabolomics. Arthritic dogs wore actiwatch during the study to collect information on changes in their activities.

Throughout the duration of the study, body weights were recorded weekly and food intake daily.

If dogs were diagnosed with diseases such as renal disease, cancer, hypothyroidism. Cushings or other disease, they were removed from the study and received treatment appropriate for their disease conditions. In addition, dogs that refused to eat at least 25% of their assigned food for more than four days or had weight loss that exceeded 2.0% weekly, were removed from the study. If any treatment was necessary to treat any other health conditions involved switching as dog to another food for more than four days, the dog was removed from the study.

The compositions used in the study are described in the table below.

TABLE 1

Nutrient composition of the feed used in the study

| Nutrient, 100% Dry Matter Basis | Canine control formula, Formula CC | Canine test formula, Formula CA |
|---|---|---|
| Crude Protein, % | 18.51 | 29.6 |
| Fat, % | 17.19 | 11.67 |
| Crude Fiber, % | 1.29 | 15.0 |
| Total Dietary Fiber, % | 7.86* | 29.4 |
| Soluble Fiber, % | 0.57* | 3.0 |
| Insoluble Fiber, % | 7.28* | 26.4 |
| Ca, % | 0.69 | 0.88 |
| P, % | 0.58 | 0.69 |
| Potassium, % | 0.55 | 0.78 |
| Magnesium, % | 0.09 | 0.17 |
| Sodium, % | 0.30 | 0.36 |
| Chloride, % | 0.66 | 0.88 |
| Lysine, % | 0.89* | 1.59 |
| Methionine, % | 0.36* | 1.29 |
| Arachidonic acid, % | 0.07* | 0.05 |
| Myristic acid, % | 0.12* | 0.49 |
| Laurate, % | 0.01* | 1.17 |
| Alpha-linolenic acid, % | 0.11* | 0.76 |
| L-carnitine, ppm | 12* | 268 |
| Lipoic acid, ppm | — | 105.43 |

*Formulated values

At baseline, arthritic dogs had significantly higher serum alkaline phosphatase levels compared to normal geriatric dogs indicating higher systemic inflammation.

TABLE 2

Serum chemistry levels at baseline

| Serum Chemistry Screen | Arthritic Dogs | Normal Dogs | Arthritis Probability* |
|---|---|---|---|
| Serum alkaline phosphatase | 220.56 | 123.14 | 0.05 |

*ANOVA-Mixed Procedure

Dogs (arthritic and normal) fed the test formula had a significant reduction in serum alkaline phosphatase, cholesterol and triglyceride levels compared to those fed the control formula.

TABLE 3

Serum chemistry levels of arthritic dogs after feeding

| Serum Chemistry Screen | Formula CA Day 0 | Formula CA Day 28 | Day 0 vs Day 28* | Formula CC Day 0 | Formula CC Day 28 | Day 0 vs Day 28* | Formula CC vs Formula CA* |
|---|---|---|---|---|---|---|---|
| Serum alkaline phosphatase | 216.28 | 118.89 | <0.01 | 224.83 | 272.78 | 0.08 | <0.01 |
| Serum cholesterol | 212.5 | 167.39 | <0.01 | 198.28 | 211.83 | 0.04 | <0.01 |
| Serum triglycerides | 171.89 | 46.83 | <0.01 | 144.17 | 129.11 | NS | <0.01 |

*ANOVA, t-test

TABLE 4

Serum chemistry levels of normal dogs after feeding

| Serum Chemistry Screen | Formula CA Day 0 | Formula CA Day 28 | Day 0 vs Day 28* | Formula CC Day 0 | Formula CC Day 28 | Day 0 vs Day 28* | Formula CC vs Formula CA* |
|---|---|---|---|---|---|---|---|
| Serum alkaline phosphatase | 118.3 | 82.2 | 0.03 | 127.55 | 133.55 | NS | 0.02 |
| Serum cholesterol | 218.7 | 179 | <0.01 | 202.36 | 203 | NS | <0.01 |

TABLE 4-continued

Serum chemistry levels of normal dogs after feeding

| Serum Chemistry Screen | Formula CA | | | Formula CC | | | Formula CC vs Formula CA* |
|---|---|---|---|---|---|---|---|
| | Day 0 | Day 28 | Day 0 vs Day 28* | Day 0 | Day 28 | Day 0 vs Day 28* | |
| Serum triglycerides | 156 | 62.9 | 0.01 | 130.82 | 94.73 | 0.09 | <0.01 |

*ANOVA, t-test

Arthritic dogs fed the test formula had significantly reduced BAP (Bone specific alkaline phosphatase) and ghrelin levels compared to dogs fed the control formula. BAP is a marker of bone formation and directly reflects osteoblast activity.

TABLE 5

Serum and urine biomarkers of arthritic dogs after feeding

| Serum Chemistry Screen | Formula CA | | | Formula CC | | | Formula CC vs Formula CA* |
|---|---|---|---|---|---|---|---|
| | Day 0 | Day 28 | Day 0 vs Day 28* | Day 0 | Day 28 | Day 0 vs Day 28* | |
| BAP, U/L | 16.4 | 12.54 | <0.01 | 20.58 | 25.22 | 0.08 | <0.01 |
| Ghrelin, ng/mL | 4.57 | 4.78 | NS | 5.29 | 5.03 | 0.08 | 0.05 |

*ANOVA, t-test

Additional changes in arthritic dogs were noted in response to the test formula, including a reduction in BAP:NTx (Bone specific alkaline phosphatase:N-terminal cross-linked telopeptide of type I collagen) ratio, and a change in night activity in response to the test formula compared to the control formula. NTx measures a cleavage product of type I collagen and reflects bone turnover or degradation.

TABLE 6

Serum and urine biomarkers of arthritic dogs after feeding

| Serum Chemistry Screen | Formula CA | | | Formula CC | | | Formula CC vs Formula CA* |
|---|---|---|---|---|---|---|---|
| | Day 0 | Day 28 | Day 0 vs Day 28* | Day 0 | Day 28 | Day 0 vs Day 28* | |
| BAP:NTx ratio | 1.38 | 1.04 | <0.01 | 1.61 | 1.93 | 0.08 | <0.01 |

*ANOVA, t-test

TABLE 7

Night activity levels of arthritic dogs

| Activity | Day | Formula CC Mean ± SE | Formula CA Mean ± SE | Formula CC vs Formula CA* |
|---|---|---|---|---|
| Night | 0 | 43.04 ± 4.38 | 45.68 ± 4.61 | NS |
| | 28 | 48.12 ± 5.59 | 41.43 ± 5.26 | NS |
| | Day 28 – Day 0 | 5.09 ± 2.48 | −4.25 ± 4.11 | 0.06 |

*ANOVA, t-test

Normal dogs fed the test formula had a significant reduction in BAP levels and BAP:NTx ratio and a significant increase in NTx levels compared to dogs fed the control formula.

TABLE 8

Serum and urine biomarkers of normal dogs after feeding

| Serum Chemistry Screen | Formula CA | | Day 0 vs Day 28* | Formula CC | | Day 0 vs Day 28* | Formula CC vs Formula CA* |
|---|---|---|---|---|---|---|---|
| | Day 0 | Day 28 | | Day 0 | Day 28 | | |
| BAP, U/L | 13.34 | 11.06 | <0.01 | 15.79 | 15.37 | NS | <0.01 |
| BAP:NTx ratio | 1.08 | 0.69 | 0.02 | 1.47 | 1.39 | NS | <0.01 |
| NTx, nM BCE | 15.1 | 17.09 | NS | 11.41 | 12.14 | NS | 0.03 |

*ANOVA, t-test

Overall, dogs (arthritic and normal) fed the test formula had decreased BAP and BAP:NTx ratio compared to dogs fed the control formula. Arthritic dogs led the test formula had decreased ghrelin levels compared to dogs fed the control formula.

TABLE 9

Serum and urine biomarkers of arthritic and normal dogs after feeding

| Serum Chemistry Screen | Formula CA | | Day 0 vs Day 28* | Formula CC | | Day 0 vs Day 28* | Formula CC vs Formula CA* |
|---|---|---|---|---|---|---|---|
| | Day 0 | Day 28 | | Day 0 | Day 28 | | |
| BAP, U/L | 16.31 | 12.01 | <0.01 | 18.76 | 21.48 | NS | <0.01 |
| BAP:NTx ratio | 1.27 | 0.91 | <0.01 | 1.56 | 1.72 | NS | <0.01 |
| Ghrelin, ng/mL | 4.43 | 4.70 | NS | 5.14 | 4.89 | 0.08 | 0.01 |

*ANOVA t-test

The results indicate that the test formula was effective to reduce bone and inflammatory conditions and thus, could be useful for the treatment of arthritis and inflammation associated with arthritis.

Example 3

Feline (Cat) Arthritis Study

A feline arthritis feeding study was conducted with 26 arthritic and 27 normal geriatric cats using similar conditions as described in Example 2.

If cats were diagnosed with diseases such as renal disease, cancer, hyperthyroidism, or other disease, they were removed from the study and received treatment appropriate for their disease conditions in addition, cats that refused to eat at least 25% of their assigned food for more than four days or had weight loss that exceeded 2.0% weekly, were removed from the study. If any treatment was necessary to treat any other health conditions involved switching a cat to another food for more than four days, the cat was removed from the study. The feline test formula was Formula FA and the feline control formula was Formula FC.

The composition of the food used for the study is provided below:

TABLE 10

Formulated nutrient profiles of the two foods utilized in the study

| Nutrients, 100% Dry Matter Basis | Feline control formula, Formula FC | Feline test formula, Formula FA |
|---|---|---|
| Crude Protein, % | 34.25 | 37.95 |
| Fat, % | 20.18 | 11.39 |
| Crude Fiber, % | 2.56 | 10.46 |

TABLE 10-continued

Formulated nutrient profiles of the two foods utilized in the study

| Nutrients, 100% Dry Matter Basis | Feline control formula, Formula FC | Feline test formula, Formula FA |
|---|---|---|
| Total dietary fiber | 4.76* | 20.05 |
| Soluble fiber, % | 0.45* | 2.62 |
| Insoluble fiber, % | 4.31* | 17.43 |
| Ca, % | 0.92 | 0.96 |
| P, % | 0.84 | 0.81 |
| Potassium, % | 0.60 | 0.80 |
| Sodium, % | 0.45 | 0.27 |
| Magnesium, % | 0.08 | 0.11 |
| Chloride, % | 0.77 | 0.73 |
| Myristic acid, % | 0.17* | 0.36 |
| Lauric acid, % | 0.01* | 0.86 |
| Alpha-linoleic acid, % | 0.14* | 1.16 |
| L-carnitine, ppm | 21* | 639 |
| Beta-carotene (ppm) | — | 3.56 |
| Methionine, % | 0.93* | 1.39 |
| Lysine, % | 1.59* | 2.12 |

*Formulated values

At baseline, arthritic cats had higher serum alkaline phosphatase and phosphorus levels but lower cholesterol levels compared to normal geriatric cats and had higher urine CTXII (Collagen type II C-terminal cross-linked fragment), serum IL-1 beta (Interleukin-beta), and serum BAP levels and lower CRII:CTXII (C-terminal pro-peptide of type II collagen:Collagen type II C-terminal cross-linked fragment) ratio compared to normal geriatric cats. CTXII measures the cross-linked C-terminal fragment of type II collagen after it has been cleaved by MMPs (matrix metallproteinases). CPU is a cleavage product of the mature type II collagen molecule which almost exclusively makes up articular cartilage, beta is a cytokine produced by activated macrophages as a proprotein and is an important mediator of the inflammatory response.

TABLE 11

Serum chemistry levels at baseline

| Serum Chemistry Screen | Arthritic Cats | Normal Cats | Arthritis Probability* |
|---|---|---|---|
| Serum alkaline phosphatase | 47.5 | 38.52 | 0.03 |
| Phosphorus | 4.44 | 4 | <0.01 |
| Cholesterol | 140.38 | 157.2 | 0.04 |

*ANOVA-Mixed Procedure

TABLE 12

Serum and urine biomarkers at baseline

| Serum Chemistry Screen | Arthritic Cats | Normal Cats | Arthritis Probability* |
|---|---|---|---|
| CTXII urine, µg/L | 7.83 | 6.18 | 0.05 |
| IL-1 beta, pg/mL | 884.94 | 351.53 | 0.03 |
| BAP, U/L | 7.83 | 6.18 | 0.05 |
| CPII:CTXII urine ratio | 53.45 | 82.51 | <0.01 |

*ANOVA-Mixed Procedure

Arthritic cats fed the test formula had significantly educed urine CPU levels, and had reduced HMGB1 levels compared to cats fed the control formula.

TABLE 13

Serum and urine biomarkers of arthritic cats after feeding

| Serum Chemistry Screen | Formula FA Day 0 | Formula FA Day 28 | Day 0 vs Day 28* | Formula FC Day 0 | Formula FC Day 28 | Day 0 vs Day 28* | Formula FC vs Formula FA* |
|---|---|---|---|---|---|---|---|
| CTXII urine, ug/L | 59.25 | 57.95 | NS | 48.54 | 32.23 | 0.01 | 0.02 |
| CPII, ng/mL | 1355.2 | 1486.9 | NS | 1274.9 | 1178.6 | NS | 0.02 |
| HMGBI, ng/mL | 0.4 | 0.34 | NS | 0.72 | 0.26 | NS | 0.07 |

*ANOVA t-test

Overall, cats (arthritic and normal) fed the test formula had decreased urine CTXII, and IGF-1 (Insulin like Growth Factor) levels and PIIANP:C2C (Procollagen type IIA N-terminal propeptide:Collgen type II C-terminal ¾ length long fragment) ratio compared to cats fed the control formula. Furthermore, cats fed the test formula had increased CPII:CTXII ratio compared to cats fed the control formula. C2C molecule is cleaved at various positions by MMPs (matrix metalloproteinases) during the degradation process of cartilage. PIIANP is also a product released during the synthesis of collagen type II molecule but reflects a different cleavage point during processing.

TABLE 14

Serum and urine biomarkers of arthritic and normal cats after feeding

| Serum Chemistry Screen | Formula FA Day 0 | Formula FA Day 28 | Day 0 vs Day 28* | Formula FC Day 0 | Formula FC Day 28 | Day 0 vs Day 28* | Formula FC vs Formula FA* |
|---|---|---|---|---|---|---|---|
| CTXII urine, ug/L | 43.8 | 40.41 | NS | 35.15 | 24.62 | <0.01 | 0.01 |
| PIIANP:C2C ratio | 5.46 | 4.52 | NS | 5.6 | 4.38 | <0.01 | 0.03 |
| IGF-1, ng/mL | 273.76 | 268.9 | NS | 268.89 | 225.92 | 0.01 | 0.02 |
| CPII:CTXII urine ratio | 64.31 | 57.18 | NS | 63.08 | 92.12 | <0.01 | 0.01 |

The results indicate that the test formula was effective to reduce bone and inflammatory conditions and thus, could be useful for the treatment of arthritis and inflammation associated with arthritis.

In view of the foregoing, the following embodiments of the invention are provided without limitation:

One embodiment of the invention provides a pet food composition that includes myristic acid, such as myristic acid from a plant source, and beta-carotene, such as beta-carotene from a plant source, in amounts effective to treat arthritis or inflammation associated with arthritis in a companion animal, such as a canine or feline. The myristic acid source may for example include or consist of coconut oil, palm oil, palm kernel oil, crystalline myristate or mixtures thereof. The beta-carotene source may, for example, include or consist of at least one of tomato pomace and carrot powder or may include or consist of kale, pumpkin, spearmint, spinach, squash and sweet potato. The amount of beta-carotene in the composition may, for example, be at least 2 parts per million (ppm), such as in the range 2-4 ppm. The pet food compositions may optionally include lipoic acid.

In one embodiment, the myristic acid is in an amount of at least about 0.1%, at least about 0.2%, and at least about 0.3%.

In one embodiment, myristic acid is at least predominantly provided by coconut oil in the composition, and beta-carotene is at least substantially provided by tomato pomace, carrot powder or mixtures thereof in the composition. In another embodiment of the invention, the amount of tomato pomace is about 2 wt % to about 8 wt %, the amount of coconut oil is about 0.5 wt % to about 6.0%, and the amount of carrot powder is about 0.1 wt % to about 2.0 wt %.

In a further embodiment, the composition includes from about 20 wt % to about $0 wt % of total protein, from about 15 wt % to about 50 wt % of total dietary fiber, and from about 3 wt % to about 15 wt % of fat.

A related embodiment of the invention provides a method for treating arthritis or inflammation associated with arthritis in a companion animal, such as a canine or feline, that includes feeding a companion animal in need of such treatment a composition of the invention. The composition may, for example, be fed to the animal as its primary or sole nutritionally complete food on a daily basis.

The composition may be fed to the animal at least once daily. The at least once daily feeding of the composition to the animal may be continued after the animal shows improvement. The composition may, for example, be fed at least once daily to the animal for at least one week, for at least one month, for at least 2 months, or for at least 3 months. As demonstrated herein, such feeding positively affects biomarkers of inflammation and bone and cartilage health. For example, such feeding reduces the serum level of alkaline phosphatase of the animal.

Another embodiment provides the use of myristic acid, such as a myristic acid plant source, for example, coconut oil, and a beta-carotene source, such as a beta-carotene plant source, for example at least one of tomato pomace and carrot powder, for the manufacture of a pet food composition, such as a nutritionally complete food, for the treatment of arthritis or inflammation associated with arthritis in a companion animal, such as a canine or a feline.

Natural plant sources of myristic acid and beta-carotene are preferred but the invention is not limited, to such sources. Corresponding embodiments to those described, but using purified or synthetic myristic acid and/or beta-carotene, are also within the scope of the invention.

What is claimed is:

1. A pet food composition comprising:
   a myristic acid source and a beta-carotene source in amounts effective to treat arthritis or inflammation associated with arthritis,
   wherein the pet food composition is a nutritionally complete pet food composition for a companion animal,
   wherein myristic acid is present in an amount of at least 0.3%, and wherein beta-carotene is present in an amount of from 2 ppm to 4 ppm,
   wherein, when fed to a canine companion animal, the pet food composition significantly reduces serum or bone specific alkaline phosphatase in the canine companion animal, and
   wherein, when fed to a feline companion animal, the pet food composition significantly increases a CPII:CTXII ratio in the feline companion animal.

2. The composition of claim 1 wherein said myristic acid source comprises coconut oil, and said beta-carotene source comprises at least one of tomato pomace and carrot powder.

3. The composition of claim 2 wherein the amount of tomato pomace is about 2 wt % to about 8 wt %; the amount of coconut oil is about 0.5 wt % to about 6.0%; and the amount of carrot powder is about 0.1 wt % to about 2.0 wt %.

4. The composition of claim 1 comprising:
   from about 20 wt % to about 50 wt % of total protein;
   from about 15 wt % to about 50 wt % of total dietary fiber; and
   from about 3 wt % to about 15 wt % of fat.

5. The composition of claim 1, further comprising lipoic acid.

6. A method for treating arthritis or inflammation associated with arthritis in a companion animal comprising;
   feeding to a companion animal in need of such treatment a nutritionally complete pet food composition, the nutritionally complete pet food composition comprising a myristic acid source and a beta-carotene source in amounts effective to treat arthritis or inflammation associated with arthritis,
   wherein myristic acid is present in an amount of at least 0.3%, and wherein beta-carotene is present in an amount of from 2 ppm to 4 ppm,
   wherein, when fed to a canine companion animal, the nutritionally complete pet food composition significantly reduces serum or bone specific alkaline phosphatase in the canine companion animal; and
   wherein, when fed to a feline companion animal, the nutritionally complete pet food composition significantly increases a CPII:CTXII ratio in the feline companion animal.

7. The method of claim 6, wherein the nutritionally complete pet food composition is fed to the companion animal at least once daily.

8. The method of claim 7, wherein the nutritionally complete pet food composition is fed at least once daily to the companion animal for at least one week.

9. The method of claim 8, wherein the nutritionally complete pet food composition is fed at least once daily to the companion animal for at least one month.

10. The method of claim 9, wherein the nutritionally complete pet food composition is fed at least once daily to the companion animal for at least two months.

11. The method of claim 6, wherein the companion animal is a canine or feline.

12. A method for manufacturing a pet food composition, the method comprising:
- producing a nutritionally complete pet food composition for a companion animal, wherein producing comprises:
  - adding a myristic acid source and a beta-carotene source to the nutritionally complete pet food composition in amounts effective for the treatment of arthritis or inflammation associated with arthritis in the companion animal,
  - wherein myristic acid is present in an amount of at least 0.3%, and wherein beta-carotene is present in an amount of from 2 ppm to 4 ppm,
- wherein, when fed to a canine companion animal, the nutritionally complete pet food composition significantly reduces serum or bone specific alkaline phosphatase, and
- wherein, when fed to a feline companion animal, the nutritionally complete pet food composition significantly increases a CPII:CTXII ratio.

* * * * *